[54] 3-(AMINOPROPYL)INDOLES

[75] Inventor: Henri Demarne, Herault, France

[73] Assignee: Clin Midy, Paris, France

[22] Filed: Feb. 16, 1973

[21] Appl. No.: 333,343

[30] Foreign Application Priority Data
Feb. 16, 1972 France............................ 72.05196

[52] U.S. Cl.................. 260/247.5 FP; 260/293.61; 260/376.15; 260/296 B; 424/248; 424/263; 424/267; 424/274
[51] Int. Cl.$^2$....................................... C07D 209/14
[58] Field of Search............. 260/326.15, 247.5 FP, 260/293.61, 296 B

[56] References Cited
OTHER PUBLICATIONS
Grandberg Dal, Chem. Abs. 74:53400g (1971).
Canas-Rodriguez et al. Chem Abs. 75:5690h (1971) abs. of Brit. Pat. 1220628.

Primary Examiner—Joseph A. Narcavage
Attorney, Agent, or Firm—Armstrong, Nikaido & Wegner

[57] ABSTRACT
Pharmacologically valuable 3-(aminopropyl)-indoles have the general formula

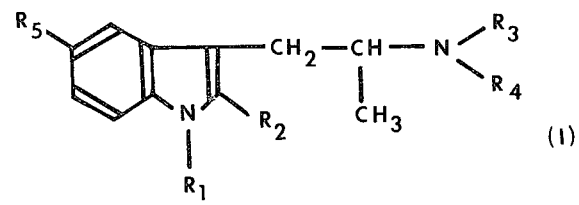

in which $R_1$ is phenyl, halophenyl, nitrophenyl, aminophenyl, loweralkoxyphenyl or pyridyl, $R_2$ is hydrogen or methyl, $R_3$ and $R_4$ are each hydrogen or lower alkyl or taken together form a polymethylene group which may be interrupted by oxygen so that $-NR_3R_4$ is a heteromonocycle having 5 or 6 nuclear atoms and $R_5$ is hydrogen, fluorine, chlorine or methoxy. Especially interesting are those compounds in which at least one of $R_1$ and $R_5$ comprises a flourine atom and $-NR_3R_4$ is pyrrolidino. The compounds are made by condensation of correspondingly substituted indolylacetones with amines $HNR_3R_4$ in a reducing medium or, in certain cases, by reduction of correspondingly substituted indolylacetoximes with or without subsequent lower alkylation.

8 Claims, No Drawings

3-(AMINOPROPYL)INDOLES

The present invention relates to indole amines, and to their preparation and use in therapeutics.

The amines to which the invention relates are those having the general formula:

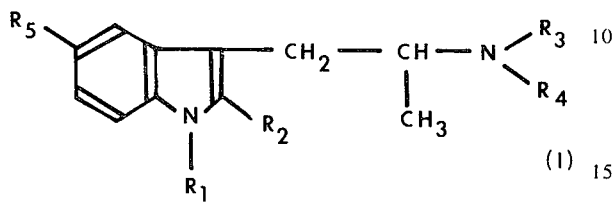

in which:

$R_1$ is a phenyl, a halophenyl, a nitrophenyl, an aminophenyl, a lower alkoxyphenyl or a pyridyl group, $R_2$ is a hydrogen atom or a methyl group, $R_3$ and $R_4$ each represent a hydrogen atom, a lower alkyl group or $R_3$ and $R_4$ taken together represent a polymethylene group which may be interrupted by an oxygen atom and the resulting heteromonocyclic group $—NR_3R_4$ having 5 or 6 nuclear atoms and $R_5$ is a hydrogen, fluorine or chlorine atom or a methoxy group. The group $—NR_3R_4$ may be a pyrrolidino, piperidino or morpholino group.

When $R_3$ and/or $R_4$ are alkyl groups they may be methyl or isopropyl groups. When $R_1$ is a halophenyl group the halogen may be fluorine or chlorine. The invention also includes the salts which these amines form with mineral and organic acids which are pharmacologically acceptable.

A preferred group of compounds in accordance with the present invention are those in which $R_1$ is a phenyl or fluorophenyl group, $R_2$ is a hydrogen atom, the group $—NR_3R_4$ is a pyrrolidino group and $R_5$ is a hydrogen, fluorine or chlorine atom.

The amines to which the invention relates are more particularly those identified in Table 1 below and among these there may be mentioned 1-(4-fluorophenyl)-3-(2-pyrrolidinopropyl)indole and its hydrochloride, 1-(4-fluorophenyl)-3-(2-pyrrolidinopropyl)-5-chloroindole and its acid fumarate, 1-phenyl-3-(2-pyrrolidinopropyl)-5-fluoroindole and 1-(4-fluorophenyl)-3-(2-pyrrolidinopropyl)-5-fluoroindole and its acid fumarate.

The invention also includes a process of preparing the amines of the invention according to which an indolyl acetone having the general formula:

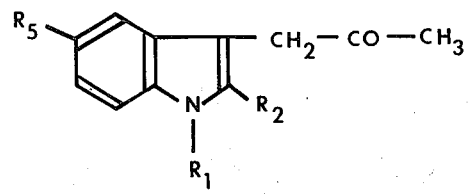

in which $R_1$, $R_2$ and $R_5$ are as above defined, is reacted in a reducing medium with an amine having the general formula

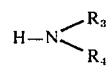

in which $R_3$ and $R_4$ are as above defined. The medium may be rendered reducing by means of formic acid or hydrogen used in the presence of a catalyst such as palladium on a carbon substrate or Raney nickel.

In a modification of the process, the indolyl acetone may be converted into the corresponding oxime, using hydroxylamine for example, the oxime reduced by means of lithium aluminium hydride and, if desired, the resulting primary amine may be subjected to alkylation when one or both of the groups $R_3$ and $R_4$ are lower alkyl groups.

In general, such substances may be obtained in accordance with the diagram below, the symbols having the meanings set forth above.

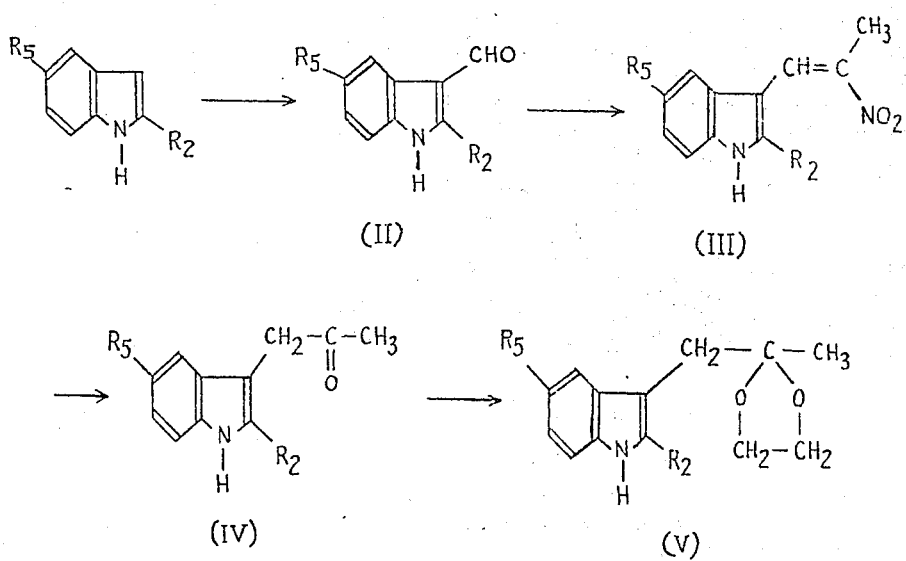

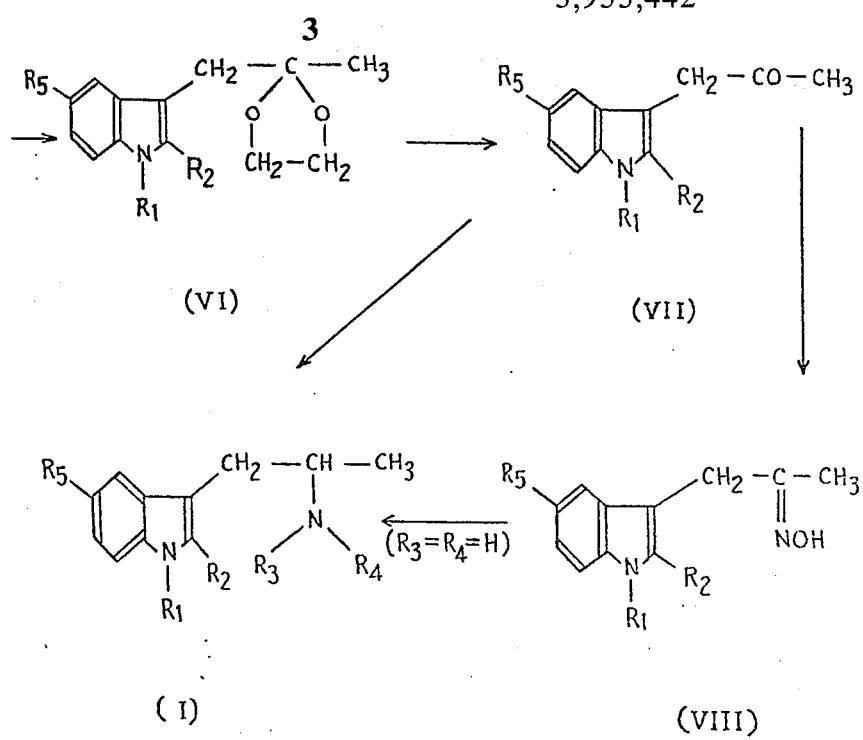

The intermediates steps VI to VIII are, as far as we are aware, novel.

The 3-(2-oxopropyl)indole (IV) may be obtained in three stages by means of three-part formylation reaction (Vilsmeyer) of a suitably substituted indole, then by reaction of nitroethane with the 3-formylindole thus obtained (II) and finally by reduction of the intermediate nitro compound (III) using iron and acetic acid. The acetalisation of the keto group may then be carried out using the conventional ethylene glycol method to give the compounds (V).

When $R_1$ designates one of the said substituted or an unsubstituted phenyl group or a pyridyl group, the group $R_4$ may be attached to the nuclear nitrogen atom by reaction of compound (V) with the corresponding halogen derivative $R_1$ — Hal, in the presence of copper powder and sodium carbonate, under reflux in a solvent having a high boiling point.

The compounds VI are thus obtained which may then be deacetalised by the action of a dilute mineral acid, thus giving the compounds VII.

The amines obtained give with organic and mineral acids salts which, in general, are soluble in water.

The following examples illustrate the invention: the melting points of the bases or their salts are marked "c" when they are determined in capillary tubes and K when they are determined using a Kofler block: the boiling points given correspond to those of the heating baths.

EXAMPLE 1 a. 5-chloro-3-formylindole 18.5 g (0.12 mole) of phosphorus oxychloride are added to 75 ml of dry dimethylformamide at 5°C. 15.15 g (0.1 mole) of 5-chloroindole dissolved in 30 ml of dry dimethylformamide are then added at 5°C. This is stirred for 30 minutes at 20°C, then for 30 minutes at 40°C. 240 ml of water followed by 72 ml of 40% soda are then quickly added. The yellow solution obtained is maintained at 40°–45°C for one hour. After 1½ hours stirring at ambient temperature the precipitate formed is filtered off and recrystallised from ethyl alcohol.

Weight of product = 13.1g Yield 74.5%. M.pt. (c) = 214°–216°C.

b. 5-chloro-3-(2-nitropropen-1-yl)indole 12.9 g of 5-chloro-3-formylindole and 1.3 g of ammonium acetate are suspended in 26 ml of nitroethane and refluxed for 1 hour. After the whole of the reactants have dissolved a mass of orange crystals are seen to form. The reaction mixture is then cooled and filtered after dilution with di-isopropyl ether. The product is recrystallised from 96% ethyl alcohol.

Weight of product = 13.9g Yield 92%. M.pt. (c) = 203°C (decomposition).

c. 5-chloro-3-(2-oxopropyl)indole

A mixture of 104g of 5-chloro-3-(2-nitropropen-1-yl)indole, 115g of powdered iron and 6g of ferric chloride dissolved in 1250 ml of acetone is brought to reflux. Heating ceases as soon as reflux commences and a solution of 265 ml of acetic acid in 800 ml of water is added over 30 minutes. The reaction mixture is again brought to reflux and maintained thereat for 4 hours; 25.6g of sodium bisulphite are then added, the mixture cooled to 20°C and filtered. The residue is washed with acetone. The combined filtrate and washings are concentrated after filtering and redissolved in 105 ml of hydrochloric acid and 520 ml of water, extracted with ethyl acetate, washed and dried.

87.5 g of oil are obtained by concentration B.pt : 183°–198°C/0.3 m.m. Weight of product 63.4 g.

The oil obtained then crystallises.

M.pt. (c) = 71°C(di-isopropyl ether).

d. 5-chloro-3-[2-(1,3-dioxolan-2-yl)propyl]indole 38g (0.61 mole) of ethylene glycol and 1.4 g of para-toluene sulphonic acid are added to 6.35g of 5-chloro-3-(2-oxopropyl)indole dissolved in 320 ml of anhydrous benzene. This mixture is brought to reflux and held thereat for 3 hours, the water formed being separated. The reaction mixture is dissolved in an aqueous solution of sodium bicarbonate and filtered to eliminate the insoluble material. The organic phase is decanted, dried and concentrated. The product obtained is recrystallised from ethanol.

Weight of product = 56g M.pt. (k) = 110°C.

e.

5-chloro-1-(4-fluorophenyl)-3-[2-(1,3-dioxolan-2-yl)propyl]indole

A mixture of 15g (0.067 mole) of 5-chloro-3-[2-(1,3-dioxolan-2-yl)propyl]indole, 225 ml of anisole, 30g (0.135 mole) of 4-fluoroiodobenzene, 30g of copper powder and 60g of dry sodium carbonate are heated to reflux for 96 hours.

The mixture is filtered when cold, then concentrated and the residue distilled.

B.pt = 220°-235°C/0./m.m. Weight of product = 18.8g.

Recrystallisation is carried out from light petroleum. M.pt. (c) = 69°C. Weight of recrystallised product = 14.5g.

f. 5-chloro-1-(4-fluorophenyl)-3-(2-oxo-propyl)indole

A mixture of 14g of 5-chloro-3-[2-(1,3-dioxolan-2-yl)propyl]-1-(4-fluorophenyl)indole, 112 ml of 96% ethyl alcohol, and 12 ml of 6N hydrochloric acid are heated to reflux for 30 minutes. The reaction mixture is concentrated then dissolved in water and extracted with ether. The organic phase is washed in water, dried, concentrated and then distilled.

B.pt — 210°-220°C/0.1 m.m. Weight of product = 12.2g.

Recrystallisation is carried out from diisopropyl ether.

Weight of product = 8g. M.pt. (c) = 51°C.

g.

5-chloro-1-(4-fluorophenyl)-3-(2-pyrrolidinopropyl)indole (code number 6112) and its acid fumarate 4.8 ml of formic acid are added at room temperature to 2.4g of 5-chloro-1-(4-fluorophenyl)-3(2-oxo-propyl)indole dissolved in 4.8 ml of pyrrolidine. An exothermic reaction occurs. Heating is then carried out for 6 hours at 130°-140°C while 4.8 ml of formic acid is gradually added in small quantities. The water formed is continuously distilled. The reaction mixture is dissolved in water, the aqueous solution extracted with ether and the aqueous phase made alkaline with sodium carbonate.

The aqueous layer is again extracted with ether, the organic phase separated, dried and concentrated under reduced pressure. The residual oil is distilled.

B.pt — 200°-230°C/0.2 m.m. Weight of product = 2.1g of yellow oil.

1.95g of this oil is dissolved hot in 20 ml of isopropanol. 0.65g of fumaric acid is added and the product filtered out.

The fumarate crystallises on cooling. M.pt. (c) = 116°-118°C.

EXAMPLE 2

1-(4-methoxyphenyl)-3-(2-isopropylaminopropyl)indole (code number 5774) and its hydrochloride 5.6g (0.02 mole) of 1-(4-methoxyphenyl)-3-(2-oxopropyl)indole dissolved in 100 ml of ethanol are poured into a 500 ml autoclave and 12.5 ml (0.2 mole) of isopropylamine and 3g of freshly prepared Raney nickel are added. The resulting mixture is placed under a pressure of 50 bars of hydrogen and is stirred at 100°C for 8 hours. The reaction mixture is filtered to remove the catalyst and the solvent is distilled under reduced pressure. The residue is dissolved in dilute hydrochloric acid and extracted with ether. The aqueous phase is neutralised with ammonia (1N). The amine is extracted with ether and distilled after removing the solvent.

B.pt. = 240°-250°C/0.5 m.m.

The oil obtained, which is dissolved in ether, is treated with hydrochloric acid gas. The viscous hydrochloride precipitate is recrystallised from isopropanol.

M.pt (k) = 200°-202°C.

EXAMPLE 3 a.

1-(2-chlorophenyl)-3-(2-hydroxyiminopropyl)indole 2.1g (0.03 mole) of hydroxylamine hydrochloride and 2.1g of sodium acetate dissolved in 10 ml. of water are added to 5.8g (0.02 mole) of 1-(2-chlorophenyl)-3-(2-oxopropyl)indole dissolved in 50 ml of ethyl alcohol. Stirring is carried out overnight at room temperature, the oxime which has precipitated is filtered (without heat), washed with water and dried. It is recrystallised from 30 ml of di-isopropyl ether.

Weight of product = 4.3g M.pt (k) = 127°C.

b. 1-(2-chlorophenyl)-3-(2-aminopropyl)indole (Code No. 6100

The oxime obtained as described under a) is reduced with lithium aluminium hydride in the following manner:

0.052 mole of 1-(2-chlorophenyl)-3-(2-hydroxyiminopropyl)indole is dissolved in 150 ml of dry tetrahydrofuran. 6 gms of lithium aluminium hydride are slowly added whilst refluxing for 3.5 hours. The reaction mixture is then poured on to a mixture of ice and ammonia and the product extracted with ether. The ethereal extract is treated with an N hydrochloric acid solution. The latter is then rendered alkaline with N soda solution. The turbid substance formed is extracted with ether, washed with water and dried. On removing the solvent the primary amine is obtained which, after recrystallisation from di-isopropyl ether, had a melting point of 79°C.

EXAMPLES 4 to 52

By proceeding in general accordance with Example 1 or in accordance with Example 2 (Examples 5, 9, 14, 26, 27 and 35) or in accordance with Example 3 (Examples 37 and 44,) and by performing the catalytic reduction of the appropriate p-nitro compound using palladium on a carbon substrate in the case of Example 20, the various compounds are obtained which are identified below in Table 1 by the definitions attributed to the symbols in formula 1 and by the melting or boiling point of the base or of one of its salts; the compounds of Examples 1 to 3 are repeated in Table 1.

TABLE 1

| Code No. | Example No. | R$_1$ | R$_2$ | R$_3$ | R$_4$ (or R$_3$ and R$_4$ taken together) | R$_5$ | Base or salt | M.pt.°C k = Kofler c = capillary | Recrystallising solvent |
|---|---|---|---|---|---|---|---|---|---|
| 5478 | 4 |  | H | | —(CH$_2$)$_5$— | H | HCl (dec) | k.240–242° | Isopropanol |
| 5479 | 5 | do. | H | H | CH$_3$ | H | do. | k.201° | do. |
| 5480 | 6 | do. | H | | —(CH$_2$)$_4$— | H | do. | k.206° dec | do. |
| 5481 | 7 | do. | H | | —CH$_2$—CH$_2$—O—CH$_2$—CH$_2$— | H | do. | k.233° dec | do. |
| 5483 | 8 | do. | H | CH$_3$ | CH$_3$ | H | do. | k.202° | do. |
| 5772 | 9 |  | H | H | CH$_3$ | H | do. | k.203° | do. |
| 5773 | 10 | do. | H | CH$_3$ | CH$_3$ | H | do. | k.194° | do. |
| 5774 | 2 | do. | H | H | —CH(CH$_3$)$_2$ | H | do. | k.200–202° | do. |
| 5775 | 11 |  | H | | —(CH$_2$)$_4$— | H | do. | k.178–180° | do. |
| 5776 | 12 | do. | H | | —(CH$_2$)$_5$— | H | base | k.98° | di-isopropyl ether |
| 5777 | 13 | do. | H | | —CH$_2$—CH$_2$—O—CH$_2$—CH$_2$— | H | do. | k.86° | do. |
| 5859 | 14 |  | H | H | CH$_3$ | H | HCl | k.192° | isopropanol |
| 5860 | 15 | do. | H | CH$_3$ | CH$_3$ | H | do. | k.252° | do. |
| 5861 | 16 | do. | H | | —(CH$_2$)$_4$— | H | do. | k.216° | acetonitrile |
| 5862 | 17 |  | H | | —(CH$_2$)$_4$— | H | do. | k.202° | isopropanol/ ethyl acetate |
| 5863 | 18 | do. | H | H | CH$_3$ | H | do. | k.127° | ethanol/ isopropanol |
| 5864 | 19 | do. | H | CH$_3$ | CH$_3$ | H | do. | k.241° | isopropanol |
| 5935 | 20 |  | H | H | CH$_3$ | H | DiHCl | k.240° | ethanol |
| 5984 | 21 |  | H | | —(CH$_2$)$_4$— | H | HCl | k.208°(subl.) | acetonitrile |
| 5987 | 22 | do. | H | CH$_3$ | CH$_3$ | H | do. | k.184° | diethyl ether /isopropanol |
| 5988 | 23 |  | H | | —(CH$_2$)$_4$— | H | do. | k.168–169° | diethyl ether /acetonitrile |
| 6044 | 24 |  | H | | —(CH$_2$)$_4$— | H | do. | c.169–170° | diethyl ether /isopropanol |
| 6049 | 25 |  | H | CH$_3$ | CH$_3$ | H | do. | k.181° | isopropanol |
| 6050 | 26 | do. | H | H | CH$_3$ | H | HCl | k.176° | do. |
| 6051 | 27 |  | H | H | CH$_3$ | H | do. | k.185° | do. |
| 6066 | 28 |  | H | | —(CH$_2$)$_4$— | CH$_3$O— | AF | c.130–131° | do. |
| 6086 | 29 | do. | H | | —(CH$_2$)$_4$— | Cl | do. | c.146–148° | do. |
| 6087 | 30 | do. | CH$_3$ | | —(CH$_2$)$_4$— | Cl | HCl | c.236° dec. | do. |
| 6088 | 31 |  | H | | —(CH$_2$)$_4$— | Cl | AF | c.181° | ethanol |
| 6097 | 32 |  | H | CH$_3$ | CH$_3$ | H | DiHCl | k.182° | isopropanol |

TABLE 1-continued

| Code No. | Example No. | R₁ | R₂ | R₃ | R₄ (or R₃ and R₄ taken together) | R₅ | Base or salt | M.pt.°C k = Kofler c = capillary | Recrystallising solvent |
|---|---|---|---|---|---|---|---|---|---|
| 6099 | 33 | 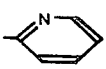 | H | CH₃ | CH₃ | H | HCl | k.162° | ethyl acetate /isopropanol |
| 6100 | 3 | 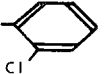 | H | H | H | H | Base | c.79° | di-isopropyl ether |
| 6102 | 34 | 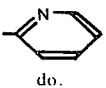 | H | | —(CH₂)₄— | H | do. | c.108° | isopropanol |
| 6104 | 35 | do. | H | H | CH₃ | H | do. | k.170° | diethyl ether /isopropanol |
| 6109 | 36 |  | CH₃ | | —(CH₂)₄— | CH₃O— | AF | c.203–205° | isopropanol |
| 6171 | 37 | 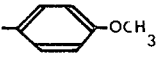 | H | H | H | H | HCl | k.189° | do. |
| 6172 | 38 | 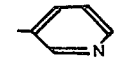 | H | | —(CH₂)₄— | H | HCl | c.213° | do. |
| 6112 | 1 | 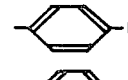 | H | | —(CH₂)₄— | Cl | AF | c.116–118° | do. |
| 6116 | 39 | 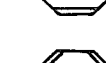 | H | | —(CH₂)₄— | F | do. | c.153–154° | acetone |
| 6091 | 40 | 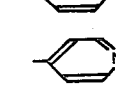 | H | | —(CH₂)₄— | Cl | HCl | c.206–207° | isopropanol |
| 6237 | 41 | 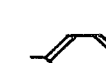 | H | | —(CH₂)₄— | H | DiHCl | k.239° | isopropanol /ethyl acetate |
| 6250 | 42 | 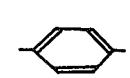 | H | | —(CH₂)₄— | F | Oxalate | c.124–125° | ethanol |
| 6251 | 43 | 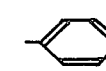 | H | | —(CH₂)₄— | F | AF | k.174° | acetone |
| 6254 | 44 | 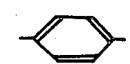 | H | H | H | H | Base | c.81° | di-isopropyl ether |
| 6264 | 45 | 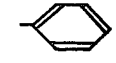 | H | CH₃ | CH₃ | F | AF | k.189° | ethanol |
| 6265 | 46 | 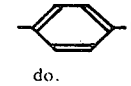 | H | CH₃ | CH₃ | F | do. | c.133–134° | acetone |
| 6268 | 47 | 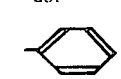 | H | CH₃ | CH₃ | Cl | do. | c.182° | ethanol |
| 6269 | 48 | do. | H | CH₃ | CH₃ | F | do. | c.185° | ethanol |
| 6270 | 49 | do. | H | | —(CH₂)₄— | CH₃O | do. | c.163–165 | acetone |
| 6271 | 50 | 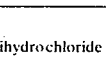 | H | CH₃ | CH₃ | CH₃O | do. | c.173–174 | acetone |

In the above table
HCl = hydrochloride  DiHCl = dihydrochloride  AF = acid fumarate Tables II to VII given below indicate the melting points of various new intermediate compounds which are used in preparing examples 1 to 52 and are identified by the definitions attributed to the symbols in a general formula

TABLE 2

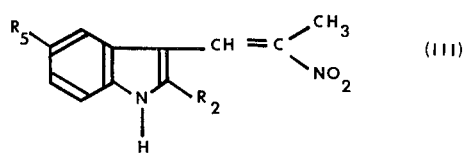

| $R_2$ | $CH_3$ | H | H | H | H |
|---|---|---|---|---|---|
| $R_5$ | Cl | Cl | $CH_3O$ | F | $CH_3O$ |
| Mpt°C | c.198°(dec) | c.203°(dec) | c.181–183° | k.181° | k.142° |
| Solvent | ethanol | 96% ethylic alcohol | Methanol | ethyl acetate | benzene |

TABLE III

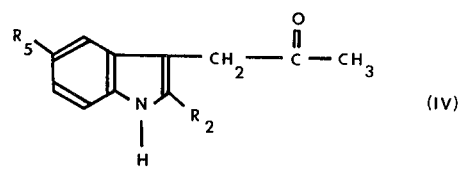

| $R_2$ | $CH_3$ | H | H |
|---|---|---|---|
| $R_5$ | Cl | $CH_3O$ | Cl |
| Mpt°C | c.111–112° | c.105–107° | c.71° |
| Solvent | di-isopropyl ether | methanol | di-isopropyl ether |

TABLE IV

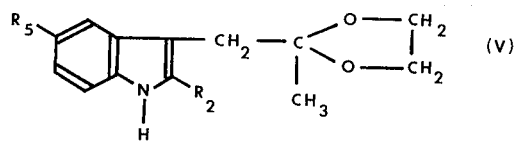

| $R_2$ | H | $CH_3$ | H | H | $CH_3$ | H |
|---|---|---|---|---|---|---|
| $R_5$ | H | Cl | $CH_3O$ | Cl | $CH_3O$ | F |
| Melting point | k.105 | c.179° | c.111–113° | c.108° | c.109–111° | k.103° |
| Solvent | di-isopropyl ether | ethanol | ethanol | ethanol | di-isopropyl ether | di-isopropyl ether |

TABLE V

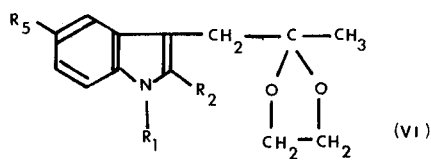

| $R_1$ | $R_2$ | $R_5$ | M.pt(°C) or B.pt E°C/m.m | Solvent |
|---|---|---|---|---|
| phenyl | H | H | 210–215°/0:1 m.m. | |
| do. | H | $CH_3O$ | 235–240°/0:2 m.m | |
| do. | H | Cl | c.82° | DIPE |

TABLE V-continued

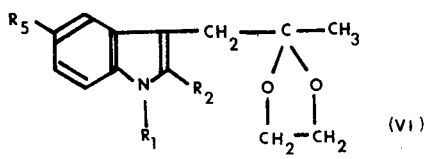
(VI)

| $R_1$ | $R_2$ | $R_5$ | M.pt(°C) or B.pt E°C/m.m | Solvent |
|---|---|---|---|---|
| do. | $CH_3$ | Cl | c.116° | DIPE |
| do. | $CH_3$ | $CH_3O$ | c.77–79° | hexane |
| 4-F-C₆H₄ | $CH_3$ | Cl | c.100° | DIPE |
| do. | H | Cl | c.69° | LP |
| do. | H | H | c.74° | DIPE |
| 4-Cl-C₆H₄ | H | H | c.105° | DIPE |
| do. | H | Cl | c.79° | LP |
| 2-F-C₆H₄ | H | H | c.95° | DIPE |
| 4-OCH₃-C₆H₄ | H | H | c.77° | Ethanol/DIPE |
| 2-Cl-C₆H₄ | H | H | c.122° | DIPE |
| 2-NO₂-C₆H₄ | H | H | c.130° | Ethanol |
| 4-NO₂-C₆H₄ | H | H | c.142° | DIPE |
| 2-pyridyl | H | H | k.104° | DIPE |
| 3-pyridyl | H | H | 210–220°/0.1 m.m. | |
| 4-pyridyl | H | H | not isolated | |
| 2-NH₂-C₆H₄ | H | H | c.90° | DIPE |
| 4-NH₂-C₆H₄ | H | H | c.123° | DIPE |
| 4-F-C₆H₄ | H | F | 168–172°/0.1 m.m. | |
| 4-Cl-C₆H₄ | H | F | c.77° | cyclohexane |

TABLE V-continued
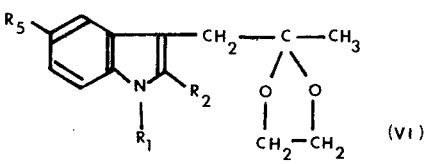
| $R_1$ | $R_2$ | $R_5$ | M.pt(°C) or B.pt E°C/m.m | Solvent |
|---|---|---|---|---|
|  —F | H | CH$_3$O | 205–210°/0.5 m.m | |
Key: DIPE = di-isopropyl ether.
LP = light petroleum
E° = Bath temperature
TABLE VI
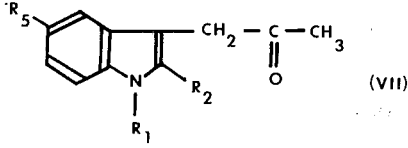
| $R_1$ | $R_2$ | $R_5$ | M.pt(°C) or B.pt E°C/m.m | Solvent |
|---|---|---|---|---|
|  | H | H | c.73° | DIPE |
| do. | H | CH$_3$O | 220–240°/0.2 | |
| do. | H | Cl | 90–91° | CH |
| do. | CH$_3$ | Cl | c.92° | CH |
| do. | CH$_3$ | CH$_3$O | 200–230°/0.1 | |
| do. | H | F | c.92–94° | DIPE |
| —F | H | H | c.55–58° | DIPE |
| 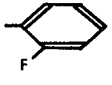 | H | H | 210–220°/0.1 | |
| 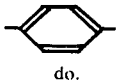—F | CH$_3$ | Cl | c.83–85° | DIPE |
| do. | H | Cl | c.51° | DIPE |
| —Cl | H | H | 220–230°/0.1 | |
| —Cl | H | Cl | c.94° | DIPE |
| 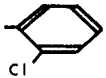 | H | H | 210–220°/0.1 | |
|  | H | H | 200–205°/0.1 | |
| 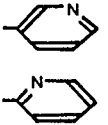 | H | H | 170–180°/0.1 | |
|  | H | H | 170–180°/0.1 | |

TABLE VI-continued
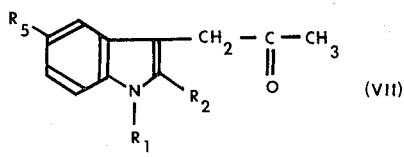
(VII)
| $R_1$ | $R_2$ | $R_5$ | M.pt(°C) or B.pt E°C/m.m. | Solvent |
|---|---|---|---|---|
| 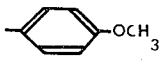 | H | H | 230–240°/0.1 | |
| do. | H | Cl | c.84–86° | methanol |
| 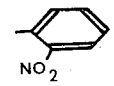 | H | H | c.77° | DIPE |
| 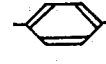 | H | H | c.90–92° | ethanol |
| 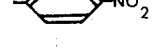 | H | H | 210–220°/0.1 | |
| 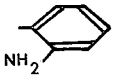 | H | H | c.135° | ethyl acetate |
| 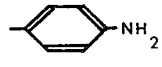 | H | F | 200–210/0.1 | |
| 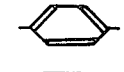 | H | F | 200–210/0.1 | |
| 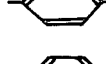 | H | $CH_3O$ | 200–250°/0.4 | |
Key : CH = cyclohexane
DIPE = di-isopropyl ether
E° = Bath temperature
TABLE VII
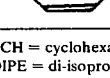
(VIII)
| $R_1$ | | M.pt(c) | Solvent |
|---|---|---|---|
|  | $R_2 = R_5 =$ H | 127°C | DIPE |
| 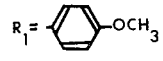 | $R_2 = R_5 =$ H | 120°C | DIPE |
Key = DIPE = di-isopropyl ether The products of the present invention have been subjected to various pharmacodynamic tests which are described below.

ANALGESIC EFFECT

The compounds (I) are analgesic agents.

A visceral pain is induced in the mouse by intraperitonal injection of a dilute solution of acetic acid (Koster and Anderson test).

The animals, which are starved on the day before the experiment and separated into random batches of 5, are treated with the products under test thirty minutes before injection of the irritant. Treatment was always performed orally.

After the acetic acid solution is injected the animals show symptoms of pain (stretching of the abdomen with extension of the back feet) which are counted during two spells of 5 minutes for each lot: from the fifth to the tenth minute and from the fifteenth to the twentieth minute respectively after the acid is injected The products are tested in increasing doses and the 50% effective dose ($ED_{50}$) which reduces by one-half the number of symptoms of pain exhibited is determined for a control batch or mice for each substance under test.

The $ED_{50}$ value is expressed in mg kg bodyweight

EFFECT ON THE CENTRAL NERVOUS SYSTEM

A brief summary is given of the tests to which batches of 6 to 10 animals are subjected per trial dose and to which a control batch which enables measured comparisons to be made is also subjected 1. Spontaneous pattern of activity.

The animals are placed in individual cages crossed by two beams which are incident upon two photoelectric cells. As they move the animals (mice) interrupt the beams and cause pulse counters to register. Variations in the motility of the treated animals is expressed as a percentage in comparison with the controls. The 50% effective dose is determined and corresponds to a decrease in activity of one half in the case of reduction in activity, and to twice as much in the case of increase in activity.

2. Traction test.

This consists of observing whether the animals (mice) can get back onto a horizontal bar held by the front feet. This test demonstrates a sedative or relaxing effect on the striated muscles.

3. Rotating bar test.

Normal animals, placed on a horizontal bar to which a rotary movement is imparted, do not fall off. This test demonstrates the balancing abilities of the normal animal, which are reduced or disappear in ataraxically treated subjects.

4. Exploration test (perforated board).

The number of holes explored by an animal (mouse) which has unrestricted movement and is placed on the board for the first time, are recorded. This test demonstrates the curiosity or, more probably, a certain state of anxiety, in an animal which is placed in an environment with which it was previously unfamiliar.

5. Anti-convulsant effect with respect to a supramaximal electric shock.

On the day before the product is tested ten mice per dose and a batch of ten control mice are subjected to a supramaximal electric shock by an alternating current at an intensity of 30 mA applied for 0.2 seconds using corneal electrodes. The animals which do not exhibit the usual reactions are removed.

The next day the batches of treated animals are subjected to the test one hour after the substance under test is administered orally.

The batch of control animals are also subjected to the electric shock to check that their sensitivity to electrical current has not altered since the previous day. When the treated animals show no reaction at 30 mA, the test is repeated ten to fifteen minutes later, at 40 mA, then again at 60,80,100 mA etc., until these reactions are observed.

TABLE VIII

| No. | ANALGESIC EFFECT $ED_{50}$ |
| --- | --- |
| 5478 | 12.5 |
| 5479 | 6.25 to 12.5 |
| 5480 | 3 to 6 |
| 5481 | 12.5 |
| 5483 | 12.5 |
| 5772 | 25 to 50 |
| 5773 | 12.5 |
| 5774 | 12.5 to 25 |
| 5775 | 25 |
| 5776 | 25 to 50 |
| 5859 | 6.25 to 12.5 |
| 5860 | 25 |
| 5861 | 25 |
| 5862 | 3.125 |
| 5863 | 6.25 |
| 5864 | 3.125 |
| 5987 | 12.5 |
| 5988 | 12.5 |
| 6050 | 6.25 to 12.5 |
| 6051 | 50 |
| 6066 | 3 to 6 |
| 6112 | 0.75 |
| 6116 | 1.5 to 3 |
| 6250 | 1.5 to 3 |
| 6251 | 12.5 |
| 6264 | 6.25 to 12.5 |
| 6265 | 6.25 to 12.5 |
| 6268 | 6.25 to 12.5 |
| 6269 | 6.25 |

TABLE IX

IP = Intraperitonal administration    PO = Oral administration    $LD_{50}$ in mg/kg

| CB No. | Spontaneous pattern of activity | Traction | Rotating rod | Exploration | Electric shock |
| --- | --- | --- | --- | --- | --- |
| 5483 | 5 IP - 25 PO | 25 IP->50 PO | 25 IP - 25 PO | 6IP - 12.5 PO | 30 PO |
| 5480 | 2.5 IP - 12.5 PO | 25 IP->50 PO | 12.5 IP - 12.5 PO | 3IP - 12.5 PO | >50 PO |
| 5481 | 2.5 IP | 100 IP | 25 IP | 30 IP | — |
| 5478 | 12.5 IP | 50 IP | 25 IP | 5 IP | — |
| 5479 | 2.5 IP - 25 PO | 25 IP - 50 PO | 25 IP - 12.5 PO | 2.5 IP - 6.25 PO | 40 PO |
| 5860 | 5 IP | 50 IP | 12.5 IP | 20 IP | 15 IP |
| 5861 | — | — | — | 25 IP | 40 IP |
| 5859 | 5 IP | 40 IP | 25 IP | 15 IP - 75 PO | 75 IP - 100 PO |
| 5935 | 2.5 IP | 50 IP | 50 IP | 50 IP | 100 IP |
| 5773 | 1.25 IP - 40 PO | 25 IP - 100 PO | 20 IP - 25 PO | 40 IP - 100 PO | 25 IP - 30 PO |
| 5775 | 1 IP | 7.5 IP | 25 IP | 5 IP | 20 IP |
| 5777 | 25 IP | 100 IP | 25 IP | >100 IP | >100 IP |
| 5776 | 5 IP - 35 PO | 25 IP->100 PO | 25 IP - 40 PO | 2.5 IP - 75 PO | 20 IP - 30 PO |

TABLE IX-continued

| IP = Intraperitonal administration | | PO = Oral administration | | | LD₅₀ in mg/kg |
|---|---|---|---|---|---|
| CB No. | Spontaneous pattern of activity | Traction | Rotating rod | Exploration | Electric shock |
| 5772 | 25 IP | 100 IP | 25 IP | 50 IP | 50 IP |
| 5774 | 12.5 IP | 50 IP | 25 IP | 20 IP | >50 IP |
| 5864 | 2 IP | 6.25 IP | 1.25 IP | 5 IP - 12.5 PO | 25 IP - 75 PO |
| 5862 | 0.4 IP | 6.25 IP | 2.5 IP | 2 IP - 6.25 PO | 70 IP - >100 PO |
| 5863 | 2 IP | 6.25 IP | 6.25 IP | 4 IP | 40 IP |
| 5987 | 6 IP - 6.25 PO | 50 IP ->100 PO | 50 IP - 100 PO | 20 IP - 100 PO | 50 IP |
| 5984 | 0.25 IP - 10 PO | 25 IP | 25 IP | 20 IP | 30 IP |
| 6051 | 5 IP | 50 IP | 50 IP | 20 IP | 100 IP |
| 5988 | 5 IP | 50 IP | 25 IP | 10 IP | >100 IP |
| 6050 | 12.5 IP | 50 IP | 50 IP | 40 IP | 50 IP |
| 6104 | 25 IP | >100 IP | 50 IP | >100 IP | 40 IP |
| 6099 | 50 IP | >50 IP | >50 IP | 25 IP | >50 IP |
| 6102 | 12.5 IP | >50 IP | >50 IP | 3.125 IP | >50 IP |
| 6097 | 10 IP | >50 IP | >50 IP | >50 IP | >50 IP |
| 6066 | 10 IP | 12.5 IP | 12.5 IP | 12.5 IP | >25 IP |
| 6112 | 0.4 IP | 6.25 IP | 3.12 IP | 2.5 IP | 100 IP |
| 6116 | 0.25 IP | 25 IP | 12.5 IP | 5.0 IP | 100 IP |
| 6250 | 0.8 IP | 3.125 IP | 3.125 IP | 1 IP | — |
|  | 3.12 PO | 12.5 PO | 12.5 PO | 3 PO | — |
| 6251 | 9 IP | 40 IP | 40 IP | 5 IP | — |
|  | 25 PO | >50 PO | >50 PO | 25 PO | — |
| 6254 | 80 IP | — | — | — | — |
| 6264 | 20 IP | >100 IP | 25 IP | 25 IP | — |
| 6265 | 20 IP | >100 IP | 25 IP | 20 IP | — |
| 6268 | 6.25 IP | 25 IP | 12.5 IP | 4 IP | — |
| 6269 | 6.25 IP | 50 IP | 25 IP | 4 IP | — |
| 6270 | 3.125 IP | 6.25 IP | 6.25 IP | 3.125 | IP — |
| 6271 | 12.5 IP | 100 IP | 50 IP | 12.5 IP | — |

The compounds of the present invention are not very toxic. By way of example, with the mouse, the dose which causes the death of 50 % of the animals or (LD₅₀) is about 400 mg/kg bodyweight by oral and sub-cutaneous administration in the case of 5862.

For compound 6112, the LD₅₀ value is between 400 and 800 mg/kg when administered by the sub-cutaneous route and greater than 800 mg/kg when taken by the oral route.

For compound 6116 the LD₅₀ value is greater than 1 g/kg when administered sub-cutaneously and between 800 mg and 1 g/kg when taken orally.

The substances may be used in human medicine for treating painful conditions which are either spontaneously generated or of surgical origin, psychoneurologic afflictions such as anxiety and insomnia, and psychiatric afflictions, and the invention includes medicaments containing these substances as active ingredients.

The active ingredients will preferably be present in forms suitable for oral, parenteral, local or endorectal administration, such, for example, as tablets, drops, syrups, powders, cachets, capsules, suppositories or injectable liquids.

It is, for example, possible to use tablets containing 10 to 200 mg of the compounds referred to by code numbers 5862, 6112, 6116 and 6250, and for example, tablets with 20 mg of 3-(2-pyrrolidinopropyl)-1-(4-fluorophenyl)indole hydrochloride (5862 CB) at a dosage of 1 to 4 tablets per day.

An example of a formula for tablets is as follows:

| | |
|---|---|
| 5862 CB (hydrochloride) | 20 mg |
| Lactose | 50 mg |
| Micro-crystalline cellulose | 40 mg |
| Talc | 5 mg |
| Magnesium stearate | 2.5 mg |
| Total | 117.5 mg |

An example of a formula for drops is given below:

| | |
|---|---|
| 5862 CB (hydrochloride) | 4 g |
| Methyl p-hydroxy benzoate (sodium salt) | 0.1 g |
| Water q.s. | 100 ml |

In veterinary medicine the compounds of the invention may be used to reduce the agressiveness of animals and make it easier to accustom them to new situations (transportation, change of surroundings).

I claim:

1. A 3-(aminopropyl)indole having the general formula

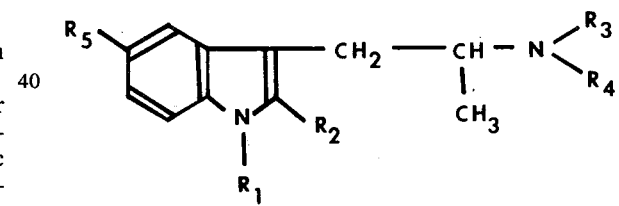

in which $R_1$ is selected from the group consisting of phenyl, halophenyl, nitrophenyl, aminophenyl, lower alkoxyphenyl and pyridyl, $R_2$ is selected from the group consisting of hydrogen and methyl, $-NR_3R_4$ is pyrrolidino, piperidino or morpholino and $R_5$ is selected from the group consisting of hydrogen, fluorine, chlorine and methoxy, together with salts of said amines with pharmacologically acceptable mineral and organic acids.

2. The 3-(aminopropyl)indole of claim 1 in which said group $-NR_3R_4$ is a pyrrolidino group.

3. The 3-(aminopropyl)indole of claim 1 in which said group $-NR_3R_4$ is a piperidino group.

4. The 3-(aminopropyl)indole of claim 1 in which said group $-NR_3R_4$ is a morpholino group.

5. The compound of claim 1 in which $R_1$ is 4-fluorophenyl, $R_2$ is hydrogen, said group $-NR_3R_4$ is pyrrolidino and $R_5$ is hydrogen, and the hydrochloride thereof.

6. The compound of claim 1 in which $R_1$ is 4-fluorophenyl, $R_2$ is hydrogen, said group $-NR_3R_4$ is pyrrolidino and $R_5$ is chlorine, and the acid fumarate thereof.

7. The compound of claim 1 in which $R_1$ is 4-fluorophenyl, $R_2$ is hydrogen, said group $-NR_3R_4$ is pyrrolidine and $R_5$ is fluorine, and the acid fumarate thereof.

8. The compound of claim 1 in which $R_1$ is phenyl, $R_2$ is hydrogen, said group $-NR_3R_4$ is pyrrolidino and $R_5$ is fluorine, and the acid fumarate thereof.

* * * * *